(12) United States Patent
Peng et al.

(10) Patent No.: US 9,239,295 B2
(45) Date of Patent: Jan. 19, 2016

(54) VARIABLE POLARIZATION WAFER INSPECTION

(71) Applicant: KLA-Tencor Corporation, Milpitas, CA (US)

(72) Inventors: Xianzhao Peng, Milpitas, CA (US); Mark Shi Wang, San Ramon, CA (US); Grace Hsiu-Ling Chen, Los Gatos, CA (US)

(73) Assignee: KLA-Tencor Corp., Milpitas, CA (US)

( * ) Notice: Subject to any disclaimer, the term of this patent is extended or adjusted under 35 U.S.C. 154(b) by 208 days.

(21) Appl. No.: 13/857,744

(22) Filed: Apr. 5, 2013

(65) Prior Publication Data

US 2013/0265577 A1 Oct. 10, 2013

Related U.S. Application Data (60) Provisional application No. 61/621,715, filed on Apr. 9, 2012.

(51) Int. Cl.
*G01N 21/88* (2006.01)
*G01N 21/21* (2006.01)
*G01N 21/95* (2006.01)

(52) U.S. Cl.
CPC ............ *G01N 21/8806* (2013.01); *G01N 21/21* (2013.01); *G01N 21/9501* (2013.01); *G01N 2021/8848* (2013.01)

(58) Field of Classification Search
None
See application file for complete search history.

(56) References Cited

U.S. PATENT DOCUMENTS

| | | | | |
|---|---|---|---|---|
| 4,512,659 A * | 4/1985 | Galbraith et al. | .......... | 356/243.1 |
| 5,078,492 A * | 1/1992 | Scheer | .......... | 356/243.1 |
| 6,034,776 A * | 3/2000 | Germer et al. | .......... | 356/369 |
| 7,623,229 B1 * | 11/2009 | Vaez-Iravani et al. | ..... | 356/237.5 |
| 8,169,613 B1 * | 5/2012 | Biellak et al. | .......... | 356/369 |
| 8,520,208 B1 * | 8/2013 | Biellak et al. | .......... | 356/369 |
| 2002/0149765 A1 | 10/2002 | Fujii et al. | | |
| 2005/0018182 A1 | 1/2005 | Hyun et al. | | |
| 2005/0018204 A1 * | 1/2005 | Li et al. | .......... | 356/493 |
| 2005/0094864 A1 * | 5/2005 | Xu et al. | .......... | 382/145 |
| 2007/0051890 A1 * | 3/2007 | Pittman | .......... | 250/332 |
| 2008/0151235 A1 | 6/2008 | Oshima et al. | | |
| 2009/0284733 A1 * | 11/2009 | Wallingford et al. | .......... | 356/73 |
| 2010/0188657 A1 | 7/2010 | Chen et al. | | |
| 2011/0320149 A1 * | 12/2011 | Lee et al. | .......... | 702/83 |

FOREIGN PATENT DOCUMENTS

KR    10-2011-0027716    3/2011

OTHER PUBLICATIONS

International Search Report and Written Opinion for PCT/US2013/035660 mailed on Jul. 1, 2013.

* cited by examiner

*Primary Examiner* — Gordon J Stock, Jr.
(74) *Attorney, Agent, or Firm* — Ann Marie Mewherter (57) ABSTRACT

Methods and systems for variable polarization wafer inspection are provided. One system includes one or more polarizing components position in one or more paths of light scattered from a wafer and detected by one or more channels of an inspection system. The polarizing component(s) are configured to have detection polarization(s) that are selected from two or more polarization settings for the polarizing component(s).

48 Claims, 3 Drawing Sheets

VARIABLE POLARIZATION WAFER INSPECTION

BACKGROUND OF THE INVENTION

1. Field of the Invention

This invention generally relates to methods and systems for variable polarization wafer inspection. Certain embodiments relate to optimizing one or more variable polarizing components for nuisance suppression.

2. Description of the Related Art

The following description and examples are not admitted to be prior an by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Currently, in dark field wafer inspection tools, polarizing components are implemented in discrete configurations in the detection channels of the tools. Two polarization directions are available: S and P. On side channels, P is defined as the polarization direction perpendicular to the scattering plane (defined by the normal line of the scattering surface and the optical axis of the collection optics), S is defined as the polarization parallel to the scattering plane and perpendicular to the optical axis of the collection optics. On the center channel, there is no well-defined scattering plane, S is defined to be parallel with the S polarization of the illumination, and P is defined to perpendicular to S and the optical axis of center channel collection optics. In this definition, P of all three channels are parallel to one another. It is noted that these definitions are different from the academic definitions of S and P polarization of scattered light and will be used throughout this document. There is also a "none analyzer" that is simply a piece of non-polarizing silica glass.

There are also three discrete polarizations that could be selected for illumination: P, S, and C (circular). So, in total, 9 polarization combinations could be selected for any given combination of an illumination channel and a detection channel on current systems. During inspection recipe setup, polarization combinations are evaluated by comparing the signal-to-noise ratio (SNR) of known defects. The polarization combination that results in the best signal to noise ratio (SNR) is chosen for the inspection recipe.

In practice, it has been shown that polarization plays a critical role in wafer inspection because of the highly polarized nature of light scattered from defects and wafer patterns. On the most difficult wafers, cross polarizations, P-S and S-P, are frequently used in illumination and detection to suppress wafer noise and enhance the SNR of defects.

The discrete polarization configurations used on current inspection systems have two limitations in defect detection. First, when the illumination is set to P polarization, S polarization for detection, in general, will not result in minimum noise from the wafer surface or pattern scattering as shown in experimental data and modeling. This limitation is an inherent result of spatial symmetry in the optical layout of illumination and collection optics, not a result of alignment or component imperfection. Hence, the SNR of defects is not truly optimized as intended.

Second, on some wafers, there are enormous amounts of nuisance defects (also referred to herein as nuisances) coexisting with the defects of interest (DOIs). On those wafers, the nuisance defects are real scattering sources but of no interest from the point of view of semiconductor process control. One example of this kind of nuisance defects is previous layer defects. Multiple types of wafers have shown this kind of issue. In general, different types of defects tend to exhibit different polarization dependencies. One potential solution to distinguish the DOIs from nuisance defects is to use polarization. But, the discrete polarization configurations on current systems significantly limit the capability of differentiating defects.

Accordingly, it would be advantageous to develop methods and systems for suppressing nuisance defects in dark field wafer inspection.

SUMMARY OF THE INVENTION

The following description of various embodiments is not to be construed in any way as limiting the subject matter of the appended claims.

One embodiment relates to a system configured to detect defects on a wafer. The system includes an illumination subsystem configured to illuminate the wafer with light having an illumination polarization. The system also includes first and second side channels configured to detect light scattered from the wafer due to illumination of the wafer by the illumination subsystem and to generate output responsive to the detected light. In addition, the system includes a first polarizing component positioned in a path of the light from the wafer detected by the first side channel and a second polarizing component positioned in a path of the light from the wafer detected by the second side channel. The first and second polarizing components are configured to have first and second detection polarizations, respectively, that are selected from two or more first and second polarization settings for the first and second polarizing components, respectively. The two or more first polarization settings include at least one first detection polarization that is asymmetric to at least one second detection polarization included in the two or more second polarization settings. The system further includes a computer subsystem configured to detect defects on the wafer based on the output generated by the at least one of the first and second side channels. The system may be further configured as described herein.

Another embodiment relates to a method for detecting defects on a wafer. The method includes illuminating the wafer with light having an illumination polarization. The method also includes detecting light scattered from the wafer due to the illuminating with first and second side channels of an inspection system and generating output responsive to the detected light. In addition, the method includes prior to detecting the light, directing the light from the wafer detected by the first side channel through a first polarizing component and directing the light from wafer detected by the second side channel through a second polarizing component. The first and second polarizing components are configured to have first and second detection polarizations, respectively, that are selected from two or more first and second polarization settings for the first and second polarizing components, respectively. The two or more first polarization settings include at least one first detection polarization that is asymmetric to at least one second detection polarization included in the two or more second polarization settings. The method further includes detecting defects on the wafer based on the output generated by the at least one of the first and second side channels.

An additional embodiment relates to a method for selecting polarization settings for an inspection system. The method includes selecting a subset of defects detected on a wafer from inspection results produced for the wafer. The subset includes one or more defects of interest (DOIs) and one or more nuisance defects. The method also includes illuminating the defects in the subset on the wafer with light having an illumination polarization. In addition, the method includes detecting light, due to the illuminating, scattered from the defects with first and second side channels of an inspection system. Detecting the light is performed for two or more first polarization settings of a first polarizing component positioned in a path of the light from the defects detected by the first side channel and two or more second polarization settings of a second polarizing component positioned in a path of the light from the defects detected by the second side channel. The two or more first polarization settings include at least one polarization that is asymmetric to at least one polarization included in the two or more second polarization settings. The first and second side channels generate output responsive to the detected light. The method further includes determining one or more characteristics of each of the defects included in the subset based on the output generated for at least two of the two or more first polarization settings and at least two of the two or more second polarization settings. The method also includes selecting at least one of the two or more first and second polarization settings for inspection of wafers by the inspection system based on the determined one or more characteristics.

Each of the steps of each of the methods described above may be performed as described further herein. The methods described above may include any other step(s) of any other method(s) described herein. The methods described above may be performed using any of the systems described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein relate generally to methodologies for optimizing polarizing components, also referred to herein as variable analyzers (VAs), in the collection optics of dark field (DF) wafer inspection tools to enhance the detection of defects of interest (DOIs) and suppression of nuisances. As will be described further herein, in this simplest form, VAs in multiple collection channels are optimized individually. In more complicated cases, VAs could be optimized in conjunction, with each channel dedicated to different roles in a complementary fashion. Studies performed on multiple wafers have demonstrated nuisance reduction by a factor of 5 to 10 times.

Figure 1:
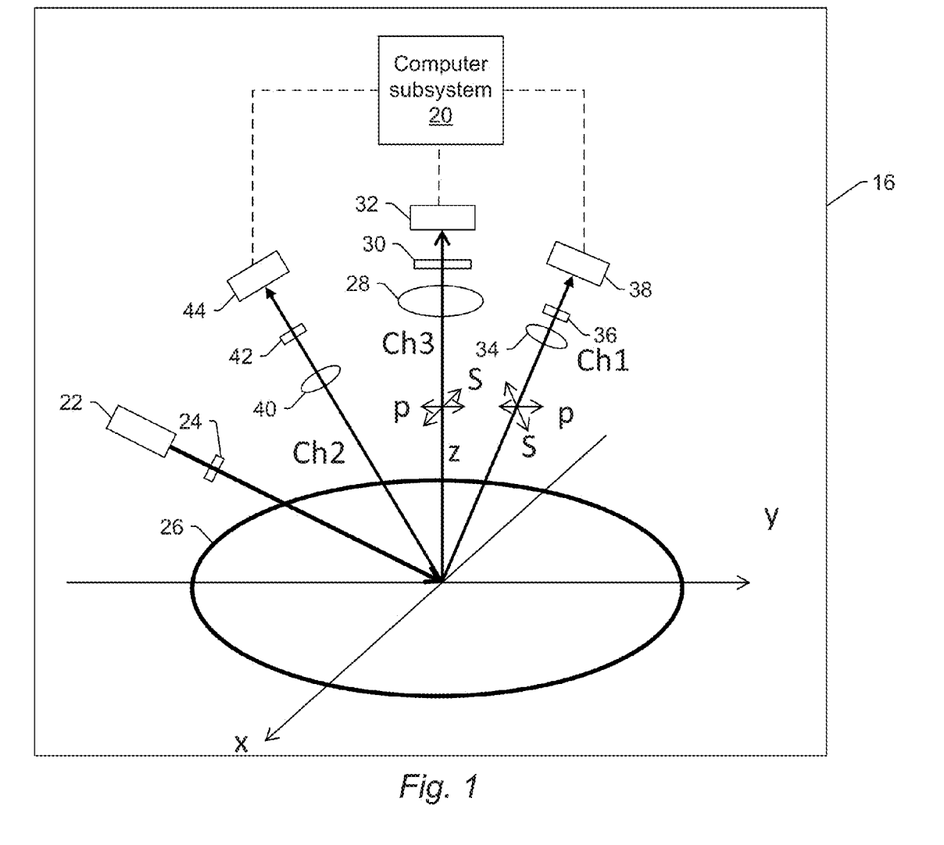
FIG. 1 is a schematic diagram illustrating a side view of one embodiment of a system configured to detect defects on a wafer.

One embodiment relates to a system configured to detect defects on a wafer. One such system is shown in FIG. 1. As shown in FIG. 1, system 16 includes an illumination subsystem configured to illuminate the wafer with light having an illumination polarization. For example, the illumination subsystem includes light source 22 such as a laser. Light source 22 is configured to direct light to polarizing component 24. In addition, the illumination subsystem may include more than one polarizing component (not shown), each of which may be positioned independently in the path of the light from the light source. Each of the polarizing components may be configured to alter the polarization of the light from the light source in a different manner. The illumination it) polarization may be P-polarized (P), S-polarized (S), or circularly polarized (C). The illumination polarization is not rotated or otherwise altered during a scan of the wafer.

Light exiting polarizing component 24 is directed to wafer 26 at an oblique angle of incidence, which may include any suitable oblique angle of incidence. The illumination subsystem may also include any other suitable optical component(s) (not shown). In addition, the illumination subsystem may be configured to direct the light to the wafer at one or more angles of incidence (e.g., an oblique angle of incidence and/or a substantially normal angle of incidence). The system may be configured to scan the light over the wafer in any suitable manner.

The system also includes one or more channels configured to detect light scattered from the wafer due to illumination of the wafer by the illumination subsystem and to generate output responsive to the detected light. In this manner, the system may be configured for DF inspection of the wafer. For example, light scattered from wafer 26 may be collected and detected by multiple channels of the system during scanning. In the embodiment shown in FIG. 1, light scattered from wafer 26 at angles relatively close to normal is collected by lens 28. Lens 28 may include a refractive optical element as shown in FIG. 1. In addition, lens 28 may include one or more refractive optical elements and/or one or more reflective optical elements. Light collected by lens 28 may be directed to polarizing component 30, which may be configured according to embodiments described further herein. In addition, the system may include more than one polarizing component (not shown), each of which may be configured according to embodiments described further herein. The system may be configured to move the polarizing components into and out of the path of the light collected by the lens in any suitable manner. The detection polarization used for the detection of the light collected by lens 28 may be selected according to embodiments described further herein.

Light exiting polarizing component 30 is directed to detector 32. Detector 32 may include any suitable detector known in the art such as a charge coupled device (CCD). Detector 32 is configured to generate output that is responsive to the scattered light collected by lens 28 and transmitted by polarizing component 30. Therefore, lens 28, polarizing component 30, and detector 32 form one channel of the inspection subsystem. In addition, since this channel is configured to collect and detect light scattered at angles relatively close to normal, the optical axis of this channel may be centered in the plane of incidence and therefore referred to as the "center" channel (Ch3) of the system shown in FIG. 1. This channel of the inspection subsystem may include any other suitable optical components (not shown) such as a Fourier filtering component.

Light scattered from wafer 26 at different angles may be collected by lens 34. Lens 34 may be configured as described above. Light collected by lens 34 may be directed to polarizing component 36, which may be configured according to embodiments described further herein. In addition, the system may include more than one polarizing component (not shown), each of which may be positioned independently in the path of the light collected by the lens. Each of the polarizing components may be configured according to embodiments described further herein. The system may be configured to move the polarizing components into and out of the path of the light collected by the lens in any suitable manner depending on which detection polarization is selected as described further herein.

Light exiting polarizing component 36 is directed to detector 38, which may be configured as described above. Detector 38 is configured to generate output that is responsive to the collected scattered light that passes through polarizing component 36. Therefore, lens 34, polarizing component 36, and detector 38 may form another channel of the system. This channel may also include any other optical components (not shown) described above. In addition, this channel may be configured as a side channel. For example, this side channel may be configured to collect and detect light that is scattered out of the plane of incidence. Therefore, lens 34, polarizing component 36, and detector 38 may form a first side channel (Ch1) of the inspection system.

The system shown in FIG. 1 also includes a second side channel. For example, the second side channel (Ch2) may include any of the optical components described herein it) such as lens 40, polarizing component 42, and detector 44, configured as a side channel. The lens, the polarizing component, and the detector may be further configured as described herein. The second side channel may be configured to collect and detect light that is scattered out of the plane of incidence. In addition, as described and shown further herein, the first and second side channels may both be configured to detect light in a plane that is substantially perpendicular to the plane of incidence. However, the first and second side channels may be centered in planes that have any other suitable angles with respect to the plane of incidence. In addition, the first and second side channels may or may not be centered in planes that have the same angles with respect to the plane of incidence.

Figure 1A:
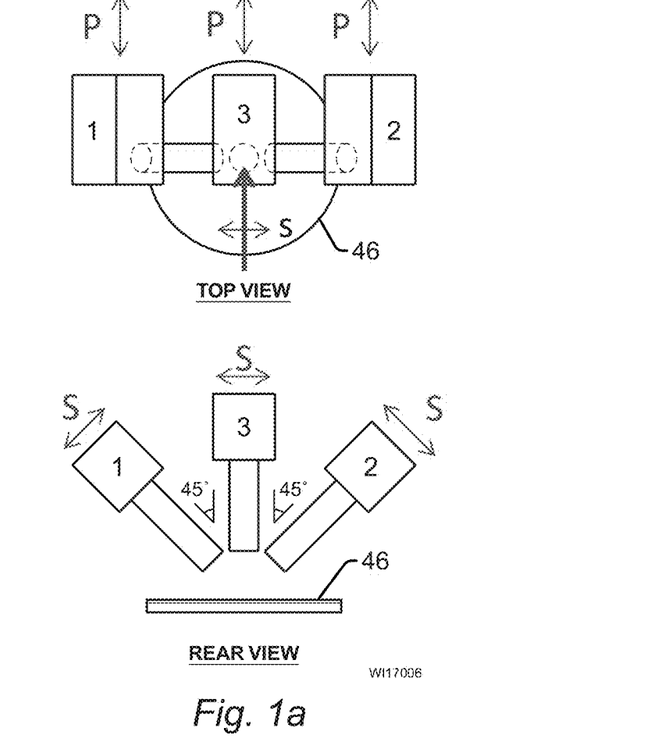
FIG. 1a is a schematic diagram illustrating a top view and a rear view of polarization definitions for one embodiment of a system described herein.

The polarization directions in the system shown in FIG. 1 may be defined as described further herein. For example, as shown in the top view of FIG. 1a, on side channels 1 and 2, P is defined as the polarization direction perpendicular to the scattering plane (defined by the normal line of scattering surface 46 and the optical axis of the collection optics). In addition as shown in the rear view of FIG. 1a, S is defined as the polarization parallel to the scattering plane and perpendicular to the optical axis of the collection optics. On center channels, there is no well-defined scattering plane, S is defined to be parallel with the S polarization of the illumination, and P is defined to be perpendicular to S and the optical axis of center channel collection optics. In this definition, P of all three channels are parallel to one another. It is noted that these definitions are different from the academic definitions of S and P polarization of scattered light and will be used throughout this document. There is also a "none analyzer" that is simply a piece of non-polarizing silica glass.

If inspection of the wafer includes more than one pass, the values of any optical parameter(s) of the system may be altered in any suitable manner if necessary between passes. For example, to change the illumination polarization states between passes, polarizing component 24 may be removed and/or replaced with a different polarizing component. In another example, to change illumination angles between passes, the position of the light source and/or any other optical components (e.g., polarizing component 24) used to direct the light to the wafer may be altered between passes in any suitable manner.

The system also includes a computer subsystem configured to detect defects on the wafer based on the output generated by at least one of the one or more channels (e.g., at least one of the first and second side channels). For example, computer subsystem 20 is configured to acquire the output generated by the channel(s). In particular, the computer subsystem may be coupled to each of the detectors (e.g., by one or more transmission media shown by the dashed lines in FIG. 1, which may include any suitable transmission media known in the art) such that the computer subsystem may receive the output generated by the detectors. The computer subsystem may be coupled to each of the detectors in any suitable manner. The output generated by the detectors during scanning of the wafer may include signals, data, image signals, image data or any other suitable output. The computer subsystem may be configured to detect the defects by applying a defect detection algorithm to the output, and the defect detection algorithm may include any suitable defect detection algorithm and/or method known in the art. The computer subsystem may also be configured to detect the defects on the wafer according to any of the embodiments described herein. The computer subsystem and the system may be configured to perform any step(s) of any method embodiment(s) described herein. The computer subsystem and the system may be further configured as described herein.

It is noted that FIG. 1 is provided herein to generally illustrate one suitable configuration of a system for detecting defects on wafers. Obviously, the system configuration described herein may be altered to optimize the performance of the system as is normally performed when designing a commercial inspection system. In addition, the systems described herein may be implemented using an existing inspection system (e.g., by adding functionality described herein to an existing inspection system) such as the Puma 90xx, 91xx, and 95xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

The system embodiments described herein include a first polarizing component positioned in a path of the light from the wafer detected by the first side channel and a second polarizing component positioned in a path of the light from the wafer detected by the second side channel. The first and second polarizing components are configured to have first and second detection polarizations, respectively, that are selected from two or more first and second polarization settings for the first and second polarizing components, respectively. For example, as shown in FIG. 1, the first polarizing component may be polarizing component 36, and the second polarizing component may be polarizing component 42. In addition, both polarizing components 36 and 42 and possibly any other polarizing components (e.g., polarizing component 30) positioned in a path of light from the wafer detected by a channel may be configured according to the embodiments described herein. The first and second detection polarizations may be selected as described further herein. As shown in FIG. 1, each of the polarizing components is positioned in only the path of light detected by one channel of the system. In other words, the first and second polarizing components are not positioned in the same optical path such that light passes through one polarizing component then the other.

Since the first and second polarizing components have two or more first and second polarization settings, respectively, the polarizing components are referred to herein as variable polarizing components in that the polarizing components provide variable polarization settings. For example, the polarizing components may be designed to provide polarization directions in a full 180 degree range. In addition, since the polarizing components are positioned in one or more detection channels of the system, the polarizing components are referred to herein as variable analyzers or VAs although the polarizing components may not be configured or used as "analyzers" as that term is commonly used in the art.

Figure 2:
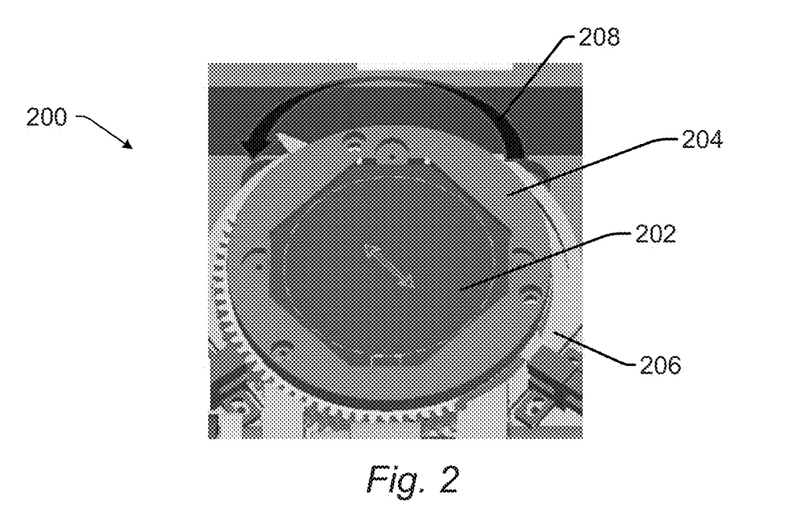
FIG. 2 is a schematic diagram illustrating a perspective view of one embodiment of a polarizing component.
Figure 3:
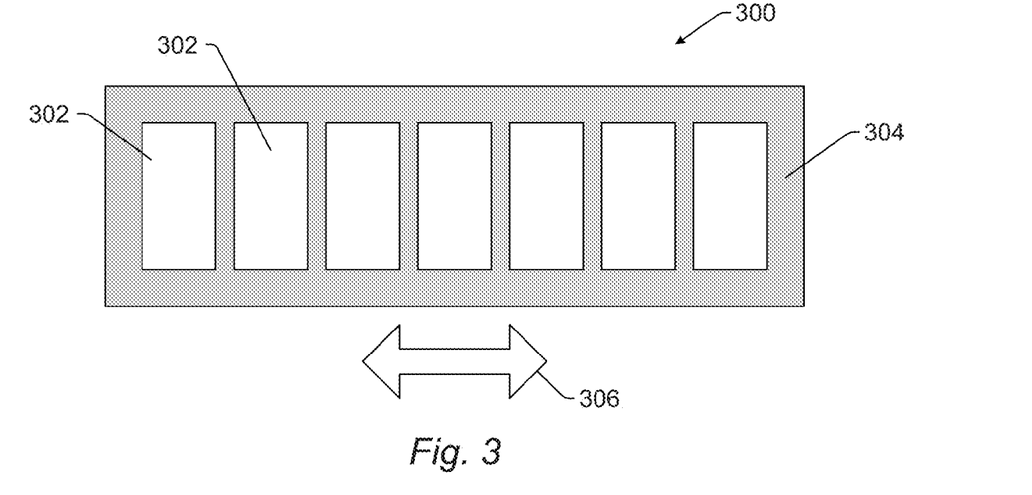
FIG. 3 is a schematic diagram illustrating a plan view of one embodiment of a polarizing component.

There are at least two mechanical approaches for the polarizing component: a rotary design and a linear design. For example, in one embodiment, at least one of the first and second polarizing components includes an analyzer and a device configured to rotate the analyzer in the path of the light from the wafer detected by at least one of the first and second channels, respectively. In the rotary design, a relatively large piece of analyzer mounted on a rotary motor allows a continuous change of polarization angle. For example, as shown in FIG. 2, polarizing component 200 includes analyzer 202 attached to mount 204, which is in turn coupled to rotary motor 206 that can rotate the mount and therefore the analyzer in direction 208. In another embodiment, at least one of the first and second polarizing components includes multiple discrete analyzers mounted side by side on a frame and a device configured to laterally translate the multiple discrete analyzers in the path of the light from the wafer detected by at least one of the first and second side channels, respectively. For example, in the linear design, multiple (e.g., 7) discrete analyzers, each with a different polarization angle (e.g., such that the change in polarization angle from one analyzer to another is some interval in degrees (e.g., 30 degrees)), are mounted on a translational frame. In one such example, as shown in FIG. 3, polarizing component 300 includes multiple discrete analyzers 302, each having a different polarization angle. Each of the analyzers is mounted on translational frame 304 that is configured to laterally translate the analyzers in directions indicated by arrow 306. In this manner, the analyzer that is positioned in the path of the light from the wafer may be altered by lateral translation depending on the detection polarization selected for inspection of the wafer. Each of the polarizing components described herein may, however, include any other suitable polarizing components known in the art.

Another embodiment relates to a method for selecting polarization settings for an inspection system. The embodiments described herein provide methodologies to optimize VA polarization settings to achieve the best suppression of nuisance detection. In the simplest form, VAs in multiple collection channels could be optimized individually. For example, in one embodiment, the first and second detection polarizations are different from each other. In another embodiment, the first and second detection polarizations are selected independently of each other. In more complicated cases, VAs could be optimized in conjunction, with each channel dedicated to different roles that are complementary to each other. For example, in some embodiments, the first and second detection polarizations are selected in combination.

In the simplest scenario, when there exists a clear difference in polarization dependency between DOIs and nuisances, each (or more than one) could be optimized individually for the best differentiation. For example, in one embodiment, the first and second detection polarizations independently and separately optimize the first and second channels, respectively, for maximum DOI detection and minimum nuisance detection.

The method includes selecting a subset of defects detected on a wafer from inspection results produced for the wafer. The subset includes one or more DOIs and one or more nuisance defects. In one embodiment, the method includes producing the inspection results for the wafer by performing a hot scan of the wafer with a nominal illumination polarization and nominal polarization settings of the first and second polarizing components. For example, in the optimization process for any one channel, the first step may be a hot scan conducted on a wafer with the analyzer(s) set at nominal P or S position corresponding to the baseline recipe. In this manner, the method may include generating a defect set by scanning a wafer with analyzer(s) set at nominal P or S position. However, the method may or may not include performing the hot scan. For example, the inspection results produced by the hot scan or any other scan can be acquired by the methods and systems described herein from another method or system or from a storage medium in which the inspection results have been stored by another method or system without actually performing the hot scan.

The hot scan is set up to catch as many defects as possible. The results of a hot scan usually contain a large number of both DOIs and nuisances from which a subset of DOIs and nuisances are selected. Preferably, the defects that are selected to be included in the subset include both DOI(s) and nuisance defect(s). In addition, the subset of to defects preferably includes fewer than all of the defects detected on the wafer and included in the inspection results. In one embodiment, selecting the subset of defects includes selecting at least one DOI and at least one nuisance defect from the inspection results based on region and intensity. In this manner, the DOIs and nuisances may be chosen to cover a variety of regions and different defect intensities. For example, selecting the defects may include selecting at least one DOI and at least one nuisance defect from each region of interest on the wafer and for different ranges of defect intensities or other characteristics of the defects. For each defect category and region, defects may be chosen in a random fashion so that the subset is a good representation of the full population.

The method also includes illuminating the defects in the subset on the wafer with light having an illumination polarization and detecting light, due to the illuminating, scattered from the defects with first and second side channels of an inspection system. The inspection system may be configured as described herein. Detecting the light is performed for two or more first polarization settings of a first polarizing component positioned in a path of the light from the defects detected the first side channel and two or more second polarization settings of a second polarizing component positioned in a path of the light from the defects detected by the second side channel, and the first and second side channels generate output responsive to the detected light. In this manner, a study of polarization dependency may be performed on the subset of defects. For each defect, images may be taken for the target die and reference dies. Unlike a wafer inspection, the illuminating and detecting steps may be performed for one defect in the subset, then the inspection system may move to the next defect in the subset and perform the illuminating and detecting steps, and so on, until output has been acquired for each defect in the subset.

The method also includes determining one or more characteristics of each of the defects included in the subset based on the output generated for at least two of the two or more first polarization settings and at least two of the two or more second polarization settings. For example, a metric of parameters may be determined for each defect in the subset. In one embodiment, the one or more characteristics include one or more of defect intensity, defect local noise, and signal-to-noise ratio (SNR), which may be the most useful parameters. Although some embodiments are described herein with respect to SNR, other characteristic(s) may be used in place of or in combination with SNR as described herein.

The one or more characteristics may be determined as a function of at least two of the two or more first polarization settings and as a function of at least two of the two or more second polarization settings. For example, the SNR dependency on VA position (VA polarization setting) of all defects studied may be plotted. The SNR of each defect may be normalized to its SNR determined using output acquired for a nominal polarization position. For example, in one embodiment, determining the one or more characteristics includes normalizing the one or more characteristics to values for the one or more characteristics determined for nominal polarization settings of the first and second polarizing components.

The method further includes selecting at least one of the two or more first and second polarization settings for inspection of wafers by the inspection system based on the determined one or more characteristics. In general, the SNR will show a clear polarization dependency on VA position. At a given VA position, the SNR of DOIs and nuisances could both be changed from a nominal polarization setting. In one embodiment, the computer subsystem of the system embodiments described herein is configured to detect the defects by applying a defect detection algorithm to the output, and, at least one of the first and second detection polarizations maximizes a number of DOIs that are detected by the applying while minimizing a number of nuisance defects that are detected by the applying.

Although embodiments are described herein with respect to selecting at least one polarization setting for at least one polarizing component positioned in the path of first and second side channels, the embodiments described herein may be used to select polarization settings for any polarizing components positioned in the path of light detected by any channel. For example, wafer inspection systems can have a variety of different channel configurations that may be significantly different from that shown in FIG. 1 (which includes a center channel and two side channels). The embodiments described herein can be used to optimize the polarization settings of any such wafer inspection systems.

In one embodiment, selecting the at least one of the two or more first and second polarization settings for the inspection includes comparing the one or more characteristics determined for the DOIs to the one or more characteristics determined for the one or more nuisance defects. If the SNR of DOIs increases more than nuisances or decreases less than nuisances, it is likely that that polarization setting would result in an inspection with a lower nuisance rate, and vice versa. The positions of the VAs (the polarization settings) that provide the largest differentiation between DOIs and nuisances may then be determined. For example, the average of the normalized SNR may be determined across all DOIs and may serve as a threshold to evaluate nuisance suppression. At a given polarization setting, the SNR of each nuisance may be compared with the threshold. If a majority of the nuisances have a normalized SNR below that threshold, the polarization setting provides a lower nuisance rate. The "score" of that VA polarization setting, defined as the ratio of the number of nuisances below the threshold over the number of nuisances above the threshold can be readily determined. The evaluation can be repeated for a number of polarization settings. The polarization setting with the highest score may be considered optimal. After the optimal polarization setting is determined, defect inspection (i.e., a preliminary inspection) can be rerun at that polarization setting. Therefore, the selecting step may be used to optimize a VA to suppress nuisance detection on an individual channel.

In one embodiment, selecting the at least one of the two or more first or second polarization settings for the inspection includes selecting one of the two or more first polarization settings for the first polarizing component and one of the two or more second polarization settings for the second polarizing component independent of each other. For example, selecting the at least one of the two or more first or second polarization settings includes, in one embodiment, selecting a first polarization setting of the first polarizing component that results in output generated by the first side channel being optimized for detection of at least some of the DOIs and suppression of the nuisance defects during the inspection and selecting a second polarization setting of the second polarizing component that results in output generated by the second side channel being optimized for at least some of the DOIs and suppression of the nuisance defects during the inspection. In this manner, VAs available on multiple channels could be optimized individually in the same way as described above. Then, all existing defect detection algorithms and/or methods can still be applied with this kind of multiple channel configuration.

In addition, this scenario, in which each channel is optimized independently of other channels in the system, can be applied to a single collection channel of a system, which may or may not include other collection channels. The single collection channel could be a center channel, and the system may not include any side channels or the method may not be performed for any side channels included in the system. Alternatively, the single collection channel could be single side channel, and the system may not include any center channels or the method may not be performed for any center channels included in the system.

The method described above represents the simplest scenario for whole system optimization. Like all polarization-based methods, it is wafer and defect type dependent. The method provides the best results when the following conditions are satisfied on a given wafer: (1) the defects in the same DOI or nuisance category exhibit relatively good consistency; (2) at least one polarization setting provides differentiation between DOIs and nuisances that is large enough to allow separation; and (3) at the selected polarization setting, the SNR of DOIs is stronger than nuisances. If any of the conditions is not satisfied, the method described above will not work very well.

However, creative strategies have been developed to deal with such challenging situations by using VAs in multiple channels. For example, the embodiments described herein can be used to configure VAs in multiple channels in a complementary way to it) achieve nuisance suppression on even the most challenging wafers. In one embodiment, selecting the at least one of the two or more first or second polarization settings for the inspection includes selecting one of the two or more first polarization settings for the first polarizing component and one of the two or more second polarization settings for the second polarizing component in combination. In this manner, instead of being individually optimized for DOIs, the VAs can be optimized in conjunction and work in a complementary fashion. Each VA may be dedicated to a different role and multiple VAs can be complementary to each other. Results combined from multiple channels can then be further filtered with a predetermined strategy to achieve an effective separation of DOIs and nuisances.

To deal with situations that do not meet conditions (1) and (2) described above, a different optimization strategy has been developed. In this case, the defects may have relatively strong SNR. However, defects in one or more DOI groups may exhibit a relatively poor consistency in polarization dependency of their one or more characteristics. Nuisances may also show similar behavior. Therefore, if one or more channels are optimized individually for the best nuisance suppression, the nuisance rate can still be at an unacceptably high level.

In one embodiment, selecting the at least one of the two or more first or second polarization settings includes selecting a first polarization setting of the first polarizing component that results in output generated by the first side channel being sensitive to the DOIs and one or more of the nuisance defects and a second polarization setting of the second polarizing component that results in output generated by the second side channel being not sensitive to the one or more nuisance defects, and the inspection includes identifying defects that are detected with the output of the first side channel and not the output of the second side channel as the one or more nuisance defects. For example, in this strategy, VAs may be first optimized individually as described above. Then, a preliminary inspection may be performed. The channel with the lower nuisance rate is chosen as the primary channel. The nuisances that are still present in the primary channel are studied on the second channel, and the polarization setting for this other channel is optimized, focusing on suppressing this smaller group of nuisances. In this manner, the method may include optimizing the polarization setting in the secondary channel to suppress the nuisances detected in the primary channel. In the final results, defects that are common to the two channels may be identified as DOIs. Defects that are unique on either one of the channels are identified as nuisances. In this manner, in one embodiment of the systems described herein, the first detection polarization results in the output generated by the first side channel being sensitive to DOIs and one or more nuisance defects, the second detection polarization results in the output generated by the second side channel being not sensitive to the one or more nuisance defects, and the computer subsystem is configured to detect the defects on the wafer by identifying the defects that are detected with the output of the first side channel and not the output of the other of the second side channel as the one or more nuisance defects.

The two or more first polarization settings include at least one first polarization (at least one first detection polarization) that is asymmetric to at least one second polarization (at least one second detection polarization) included in the two or more second polarization settings. In this manner, at least one (or each) of the VAs is capable of having a polarization that is asymmetric to the polarization of another VA although an asymmetric polarization may or may not be selected as described further herein. The at least one first detection polarization that is asymmetric to the at least one second detection polarization is not parallel to the at least one second detection polarization, perpendicular to the at least one second detection polarization, circular polarization, or an unpolarized setting. In other words, the at least one polarization included in the two or more first polarization settings that is asymmetric to the at least one polarization included in the two or more second polarization settings is not parallel to the at least one polarization included in the two or more second polarization settings, perpendicular to the at least one polarization included in the two or more second polarization settings, circular polarization, or an unpolarized setting.

The first and second detection polarizations are not rotated during inspection of the wafer. In addition, the at least one of the two or more first or second polarization settings selected for the inspection includes two or more detection polarizations that are not rotated during the inspection of the wafers. In this manner, in the system embodiments described herein, the detection polarization is not rotated during inspection of the wafer. For example, any of the polarization settings described herein may be switched between inspection of different wafers or even between different scans of the same wafer, and therefore, any of the polarization settings may be essentially rotated due to the switching of the polarizations. However, during wafer inspection or during scanning of light over the wafer for inspection purposes, the polarization setting(s) in the channels of the inspection system are not altered by rotation or otherwise. Therefore, the embodiments described herein are fundamentally different than some optical systems (e.g., rotating analyzer or rotating polarizer ellipsometers) in which measurements are made by rotating one or more polarizing components positioned in either the illumination path or the detection path to thereby rotate the polarizations of those polarizing components. For example, such systems may have illumination and detection polarizations that are asymmetric with respect to each other at some point in time during a measurement at one location of the wafer; however, those polarizations are typically continuously altered while measurements are performed at that one location, then other locations on the wafer are measured in a similar manner. In contrast, the illumination and detection polarizations of the systems and methods described herein will be set once prior to a scan of a wafer and remain constant during that scan.

The method described above tends to generate one or more detection polarizations that are asymmetric to each other. There is a good reason behind that. When the primary channel is optimized, nuisances with peaks relatively far away from the polarization setting for the primary channel will be suppressed. DOIs with peaks in the same polarization region will also suffer some loss but, in general, their SNRs are stronger than the nuisances. Therefore, fewer DOIs will be suppressed compared to the nuisance defects. Nuisances with peaks around the polarization setting of the primary channel will be kept in the primary channel result. When the persistent nuisances are examined on the secondary channel, since their peaks are in the symmetric position of the polarization setting in the primary channel, selecting the polarization setting of the secondary channel at the primary channel polarization setting would not help suppress the remaining nuisances in the secondary channel. However, if the polarization setting in the secondary channel is set at an asymmetric position to the primary channel, i.e., away from the symmetric polarization, the remaining nuisances will be effectively suppressed.

In one embodiment, selecting the at least one of the two or more first or second polarization settings includes selecting one of the two or more first polarization settings for the first polarizing component, and the method includes selecting one of the two or more second polarization settings that is asymmetric to the selected one of the two or more first polarization settings for the second polarizing component. In this manner, in the system embodiments described herein, the first and second detection polarizations may be asymmetric with respect to each other. For example, with the knowledge described above, it is predictable that a polarization setting for the secondary channel that is asymmetric to the polarization setting of the primary channel will result in the best suppression of the persistent nuisances on the primary channel. Therefore, it may be possible to skip the step of optimizing the secondary channel and directly set the polarization setting of the secondary channel asymmetric to that of the primary channel.

In situations which do not satisfy condition (3) described above, as long as there exists a relatively clear difference in polarization dependency between DOIs and nuisances, it is still possible to separate them. For example, in one embodiment, selecting the at least one of the two or more first or second polarization settings includes selecting a first polarization setting of the first polarizing component that results in output generated by the first side channel being sensitive to the DOIs and the nuisance defects and a second polarization setting of the second polarizing component that results in output generated by the second side channel being sensitive to the nuisance defects but not the DOIs, and the inspection includes identifying defects that are detected with both the output of the first and second side channels as the nuisance defects. In this manner, in one embodiment of the system described above, the first detection polarization results in the output generated by the first side channel being sensitive to DOIs and nuisance defects, the second detection polarization results in the output generated by the second side channel being sensitive to the nuisance defects but not the DOIs, and the computer subsystem is configured to detect the defects on the wafer by identifying the defects that are detected with both the output of the first and second side channels as the nuisance defects.

In one such example, DOIs and nuisances may exhibit different trends in VA dependency. By examining the SNR dependency on VA polarization setting, one might simply put the VA at the polarization setting that results in the highest SNR of DOIs or the lowest SNR of nuisances. However, a closer examination of the SNRs may reveal that the SNR of DOIs is weaker than nuisance in general. At the polarization setting that results in the maximum SNR of DOIs and minimum SNR of nuisances, their SNRs may largely overlap and therefore it would be nearly impossible to separate them at that VA polarization setting. At other polarization settings, the SNR of the DOIs may be weaker than that of the nuisances and a relatively large percentage of the DOIs may fall below the detection limit, making the DOIs undetectable.

To resolve this dilemma, two channels may be compared at their polarization settings that result in the detection of maximum DOIs in each channel, respectively. The channel with more DOIs is kept at its polarization setting and serves as the primary channel. It is configured to detect as many DOIs as possible. A significant number of nuisances will be detected as well in the primary channel since the SNRs of the nuisances are similar to the DOIs at this polarization setting. The polarization setting of the second channel is then changed to that which results in the maximum amount of nuisance detection. There will be very few DOIs detected in the output of the second channel since the SNRs of DOIs at this polarization setting are much weaker than the nuisances. In other words, the second channel is configured to detect nuisances. After inspection is run using this configuration, the defects detected by both channels are treated as nuisances. Only the unique defects detected by the primary channel will be designated as the DOIs. In this manner, the second channel (or "nuisance channel") is used to filter out the nuisances that inevitably exist in the primary channel. With this approach, the nuisance rate could be reduced by a factor greater than 5 while still keeping a relatively good capture rate of DOIs.

Again, this strategy usually results in asymmetric polarization settings on the side channels of the inspection system. The DOIs and nuisances will exhibit a relatively large and different imbalance between the two side channels as a natural outcome of the VA configuration strategy. Therefore, defect detection algorithms and/or methods that are configured to exploit different capture rates of different types of defects (a "channel imbalance" algorithm) will work effectively with this configuration.

Although some embodiments, in which two or more polarization settings for two or more polarizing components are selected in combination with each other, have been described for situations in which asymmetric polarizations available on side channels can be advantageously used to differentiate DOIs and nuisances on particularly problematic wafers, clearly, the embodiments for selecting one or more polarization settings for two or more polarizing components can be used to select, in a complementary fashion, polarization settings for any polarizing components positioned in any channels of any wafer inspection system. For example, the scenarios described above can be equally applied to any system with two channels. The two channels may be two side channels, one center channel and a single side channel, etc. In addition, the embodiments can be used to select polarization settings in systems in which none of the channels can have asymmetric polarizations with respect to each other. In other words, the embodiments described herein are not limited to wafer inspection systems that include two channels that can have asymmetric polarizations with respect to each other.

The embodiments described herein have a number of advantages over previously and currently used methods for selecting polarization settings for inspection. For example, the VAs and the methodologies to optimize their polarization settings described herein have been demonstrated to achieve a greater than 5x reduction of nuisance detection compared to existing DF wafer inspection tools or to keep the nuisance rate below 20% of total defects detected. In addition, the embodiments described herein have been demonstrated to reduce the nuisances detected on some wafers by a factor of 8 to 10 times, or one order of magnitude. When nuisance rate is reduced, an inspection recipe can be set at a higher sensitivity, up to the tool sensitivity limit, which therefore enhances DOI detection.

In addition, the analysis and optimization of the polarization settings can be completely automated. The embodiments described herein also provide much more flexible control of the detection polarization settings than existing implementations. In addition, the methods described herein provide an efficient and systematic way to optimize variable detection polarization setting(s) to best distinguish DOIs from nuisances. Furthermore, VAs installed in multiple channels of an inspection system are capable of creating channel imbalance. Combined with a channel imbalance-exploiting defect detection algorithm, the embodiments provide a powerful method to suppress nuisances in the most challenging situations. For at least these reasons, the VAs described herein may be one of the key features of the next generation of DF optical inspection tools.

Another embodiment relates to a method for detecting defects on a wafer. The method includes illuminating the wafer with light having an illumination polarization. The method also includes detecting light scattered from the wafer due to the illuminating step with first and second side channels of an inspection system and generating output responsive to the detected light. The inspection system may be configured according to any of the embodiments described herein. In addition, the method includes prior to detecting the light, directing the light from the wafer detected by the first side channel through a first polarizing component and directing the light from the wafer detected by the second side channel through a second polarizing component. The first and second polarizing components are configured to have first and second detection polarizations, respectively, that are selected from two or more first and second polarization settings for the first and second polarizing components, respectively, and the two or more first polarization settings include at least one first detection polarization that is asymmetric to at least one second detection polarization included in the two or more second polarization settings. The first and second polarizing components may be configured according to any of the embodiments described herein. The method further includes detecting defects on the wafer based on the output generated by the at least one of the first and second side channels.

Each of the steps of this method may be further performed according to any of the embodiments described herein. In addition, the method may include any other step(s) any other embodiment(s) described herein. Furthermore, the method may be performed by any of the system embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 4:
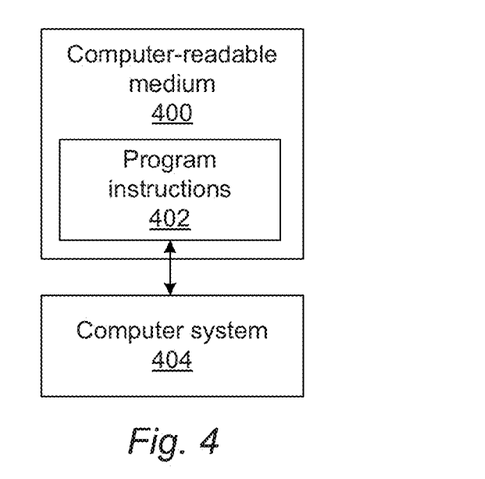
FIG. 4 is a block diagram illustrating one embodiment of a computer-readable medium storing program instructions executable on a computer system for performing one or more of the method embodiments described herein.

Another embodiment relates to a non-transitory computer-readable medium storing program instructions executable on a computer system for performing a method a computer-implemented method) for detecting defects on a wafer. One such embodiment is shown in FIG. 4. For example, as shown in FIG. 4, non-transitory computer-readable medium 400 includes program instructions 402 executable on computer system 404 for performing one or more steps of the method for detecting defects on a wafer described above.

Program instructions 402 implementing methods such as those described herein may be stored on non-transitory computer-readable medium 400. The computer-readable medium may be a storage medium such as a magnetic or optical disk, a magnetic tape or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 404 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Further modifications and alternative embodiments of various aspects of the invention will be apparent to those skilled in the art in view of this description. For example, methods and systems for variable polarization wafer inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a wafer comprising:
   an illumination subsystem configured to illuminate the wafer with light having an illumination polarization;
   first and second side channels configured to detect light scattered from the wafer due to illumination of the wafer by the illumination subsystem and to generate output responsive to the detected light;
   a first polarizing component positioned in a path of the light from the wafer detected by the first side channel and a second polarizing component positioned in a path of the light from the wafer detected by the second side channel, wherein the first and second polarizing components are configured to have first and second detection polarizations, respectively, that are selected from two or more first and second polarization settings for the first and second polarizing components, respectively, wherein the two or more first polarization settings comprise at least one first detection polarization that is asymmetric to at least one second detection polarization included in the two or more second polarization settings, wherein the first detection polarization results in the output generated by the first side channel being sensitive to defects of interest and one or more nuisance defects, and wherein the second detection polarization results in the output generated by the second side channel being not sensitive to the one or more nuisance defects; and
   a computer subsystem configured to detect defects on the wafer based on the output generated by at least one of the first and second side channels, wherein the computer subsystem is further configured to detect the defects on the wafer by identifying the defects that are detected with the output of the first side channel and not the output of the second side channel as the one or more nuisance defects.

2. The system of claim 1, wherein the at least one first detection polarization that is asymmetric to the at least one second detection polarization is not parallel to the at least one second detection polarization, perpendicular to the at least one second detection polarization, circular polarization, or an unpolarized setting.

3. The system of claim 1, wherein at least one of the first and second polarizing components comprises an analyzer and a device configured to rotate the analyzer in the path of the light from the wafer detected by at least one of the first and second side channels, respectively.

4. The system of claim 1, wherein at least one of the first and second polarizing components comprises multiple discrete analyzers mounted side by side on a frame and a device configured to laterally translate the multiple discrete analyzers in the path of the light from the wafer detected by at least one of the first and second side channels, respectively.

5. The system of claim 1, wherein the computer subsystem is further configured to detect the defects by applying a defect detection algorithm to the output, and wherein at least one of the first and second detection polarizations maximizes a number of the defects of interest that are detected by said applying while minimizing a number of the one or more nuisance defects that are detected h said applying.

6. The system of claim 1, wherein the first and second detection polarizations are different from each other.

7. The system of claim 1, wherein the first and second detection polarizations are selected independently of each other.

8. The system of claim 1, wherein the first and second detection polarizations are selected combination.

9. The system of claim 1, wherein the first and second detection polarizations independently and separately optimize the first and second side channels, respectively, for maximum defect of interest detection and minimum nuisance detection.

10. The system of claim 1, wherein the first and second detection polarizations are not rotated during inspection of the wafer.

11. The system of claim 1, wherein the computer subsystem is further configured for selecting a subset of defects detected on the wafer or another wafer from inspection results produced for the wafer or the other wafer, wherein the subset comprises one or more of the defects of interest and the one or more nuisance defects, wherein the illumination subsystem is further configured to illuminate the defects in the subset on the wafer or the other wafer with the light having the illumination polarization, wherein the first and second side channels are further configured to detect light, due to the illumination, scattered from the defects in the subset for the two or more first polarization settings and the two or more second polarization settings, and wherein the computer subsystem is further configured for determining one or more characteristics of each of the defects included in the subset based on the output generated for at least two of the two or more first polarization settings and at least two of the two or more second polarization settings and selecting at least one of the two or more first and second polarization settings for inspection of wafers by the system based on the determined one or more characteristics.

12. The system of claim 11, wherein the computer subsystem is further configured for producing the inspection results for the wafer or the other wafer by performing a hot scan of the wafer or the other wafer with a nominal illumination polarization and nominal polarization settings of the first and second polarizing components.

13. The system of claim 11, wherein selecting the subset of defects comprises selecting at least one of the defects of interest and at least one of the one or more nuisance defects from the inspection results based on region and intensity.

14. The system of claim 11, wherein the one or more characteristics comprise one or more of defect intensity, defect local noise, and signal-to-noise ratio, and wherein the one or more characteristics arc determined as a function of at least two of the two or more first polarization settings and as a function of at least two of the two or more second polarization settings.

15. The system of claim 11, wherein determining the one or more characteristics comprises normalizing the one or more characteristics to values for the one or more characteristics determined for nominal polarization settings of the first and second polarizing components.

16. The system of claim 11, wherein selecting the at least one of the two or more first or second polarization settings for the inspection comprises comparing the one or more characteristics determined for the one or more of the defects of interest to the one or more characteristics determined for the one or more nuisance defects.

17. A method for detecting defects on a wafer, comprising:
illuminating the wafer with light having an illumination polarization;
detecting light scattered from the wafer due to said illuminating with first and second side channels of an inspection system and generating output responsive to the detected light;
prior to said detecting, directing the light from the wafer detected by the first side channel through a first polarizing component and directing the light from the wafer detected by the second side channel through a second polarizing component, wherein the first and second polarizing components are configured to have first and second detection polarizations, respectively, that are selected from two or more first and second polarization settings for the first and second polarizing components, respectively, wherein the two or more first polarization settings comprise at least one first detection polarization that is asymmetric to at least one second detection polarization included in the two or more second polarization settings, wherein the first detection polarization results in the output generated by the first side channel being sensitive to defects of interest and one or more nuisance defects, and wherein the second detection polarization results in the output generated by the second side channel being not sensitive to the one or more nuisance defects; and
detecting defects on the wafer based on the output generated by at least one of the first and second side channels, wherein detecting the defects comprises identifying the defects that are detected with the output of the first side channel and not the output of the second side channel as the one or more nuisance defects.

18. A method for selecting polarization settings for an inspection system, comprising:
selecting a subset of defects detected on a wafer from inspection results produced for the wafer, wherein the subset comprises one or more defects of interest and one or more nuisance defects;
illuminating the defects in the subset on the wafer with light having an illumination polarization;
detecting light, due to said illuminating, scattered from the defects with first and second side channels of an inspection system, wherein said detecting is performed for two or more first polarization settings of a first polarizing component positioned in a path of the light from the defects detected by the first side channel and two or more second polarization settings of a second polarizing component positioned in a path of the light from the defects detected by the second side channel, wherein the two or more first polarization settings comprise at least one polarization that is asymmetric to at least one polarization included in the two or more second polarization settings, and wherein the first and second side channels generate output responsive to the detected light;

determining one or more characteristics of each of the defects included in the subset based on the output generated for at least two of the two or more first polarization settings and at least two of the two or more second polarization settings; and selecting at least one of the two or more first and second polarization settings for inspection of wafers by the inspection system based on the determined one or more characteristics.

19. The method of claim 18, wherein selecting the at least one of the two or more first or second polarization settings for the inspection comprises selecting one of the two or more first polarization settings for the first polarizing component and one of the two or more second polarization settings for the second polarizing component independent of each other.

20. The method of claim 18, wherein selecting the at least one of the two or more first or second polarization settings for the inspection comprises selecting one of the two or more first polarization settings for the first polarizing component and one of the two or more second polarization settings for the second polarizing component in combination.

21. The method of claim 18, wherein selecting the at least one of the two or more first or second polarization settings comprises selecting one of the two or more first polarization settings for the first polarizing component, the method further comprising selecting one of the two or more second polarization settings that is asymmetric to the selected one of the two or more first polarization settings for the second polarizing component.

22. The method of claim 18, further comprising producing the inspection results for the wafer by performing a hot scan of the wafer with a nominal illumination polarization and nominal polarization settings of the first and second polarizing components.

23. The method of claim 18, wherein selecting the subset of defects comprises selecting at least one defect of interest and at least one nuisance defect from the inspection results based on region and intensity.

24. The method of claim 18, wherein the one or more characteristics comprise one or more of defect intensity, defect local noise, and signal-to-noise ratio, and wherein the one or more characteristics are determined as a function of at least two of the two or more first polarization settings and as a function of at least two of the two or more second polarization settings.

25. The method of claim 18, wherein determining the one or more characteristics comprises normalizing the one or more characteristics to values for the one or more characteristics determined for nominal polarization settings of the first and second polarizing components.

26. The method of claim 18, wherein selecting the at least one of the two or more first or second polarization settings for the inspection comprises comparing the one or more characteristics determined for the one or more defects of interest to the one or more characteristics determined for the one or more nuisance defects.

27. The method of claim 18, wherein the at least one polarization included in the two or more first polarization settings that is asymmetric to the at least one polarization included in the two or more second polarization settings is not parallel to the at least one polarization included in the two or more second polarization settings, perpendicular to the at least one polarization included in the two or more second polarization settings, circular polarization, or an unpolarized setting.

28. The method of claim 18, wherein the at least one of the two or more first or second polarization settings selected for the inspection comprises two or more detection polarizations that are not rotated during the inspection of the wafers.

29. The method of claim 18, wherein selecting the at least one of the two or more first or second polarization settings comprises selecting a first polarization setting of the first polarizing component that results in output generated by the first side channel being optimized for detection of at least some of the defects of interest and suppression of the nuisance defects during the inspection and selecting a second polarization setting of the second polarizing component that results in output generated by the second side channel being optimized for detection of at least some of the defects of interest and suppression of the nuisance defects during the inspection.

30. The method of claim 18, wherein selecting the at least one of the two or more first or second polarization settings comprises selecting a first polarization setting of the first polarizing component that results in output generated by the first side channel being sensitive to the defects of interest and one or more of the nuisance defects and a second polarization setting of the second polarizing component that results in output generated by the second side channel being not sensitive to the one or more nuisance defects, and wherein the inspection comprises identifying defects that are detected with the output of the first side channel and not the output of the second side channel as the one or more nuisance defects.

31. The method of claim 18, wherein selecting the at least one of the two or more first or second polarization settings comprises selecting a first polarization setting of the first polarizing component that results in output generated by the first side channel being sensitive to the defects of interest and the nuisance defects and a second polarization setting of the second polarizing component that results in output generated by the second side channel being sensitive to the nuisance defects hut not the defects of interest, and wherein the inspection comprises identifying defects that are detected with both the output of the first and second side channels as the nuisance defects.

32. A system configured to detect defects on a wafer, comprising:

an illumination subsystem configured to illuminate the wafer with light having an illumination polarization;

first and second side channels configured to detect light scattered from the wafer due to illumination of the wafer by the illumination subsystem and to generate output responsive to the detected light;

a first polarizing component positioned in a path of the light from the wafer detected by the first side channel and a second polarizing component positioned in a path of the light from the wafer detected by the second side channel, wherein the first and second polarizing components are configured to have first and second detection polarizations, respectively, that are selected from two or more first and second polarization settings for the first and second polarizing components, respectively, wherein the two or more first polarization settings comprise at least one first detection polarization that is asymmetric to at least one second detection polarization included in the two or more second polarization settings, wherein the first detection polarization results in the output generated by the first side channel being sensitive to defects of interest and nuisance defects, and wherein the second detection polarization results in the output generated by the second side channel being sensitive to the nuisance defects but not the defects of interest; and a computer subsystem configured to detect defects on the wafer based on the output generated by at least one of the first and second side channels, wherein the computer subsystem is further configured to detect the defects on the wafer by identifying the defects that are detected with both the output of the first and second side channels as the nuisance defects.

33. The system of claim 32, wherein the at least one first detection polarization that is asymmetric to the at least one second detection polarization is not parallel to the at least one second detection polarization, perpendicular to the at least one second detection polarization, circular polarization, or an unpolarized setting.

34. The system of claim 32, wherein at least one of the first and second polarizing components comprises an analyzer and a device configured to rotate the analyzer in the path of the light from the wafer detected by at least one of the first and second side channels, respectively.

35. The system of claim 32, wherein at least one of the first and second polarizing components comprises multiple discrete analyzers mounted side by side on a frame and a device configured to laterally translate the multiple discrete analyzers in the path of the light from the wafer detected by at least one of the first and second side channels, respectively.

36. The system of claim 32, wherein the computer subsystem is further configured to detect the defects by applying a defect detection algorithm to the output, and wherein at least one of the first and second detection polarizations maximizes a number of the defects of interest that are detected by said applying while minimizing a number of the nuisance defects that are detected by said applying.

37. The system of claim 32, wherein the first and second detection polarizations are different from each other.

38. The system of claim 32, wherein the first and second detection polarizations are selected independently of each other.

39. The system of claim 32, wherein the first and second detection polarizations are selected in combination.

40. The system of claim 32, wherein the first and second detection polarizations independently and separately optimize the first and second side channels, respectively, for maximum defect of interest detection and minimum nuisance detection.

41. The system of claim 32, wherein the first and second detection polarizations are not rotated during inspection of the wafer.

42. The system of claim 32, wherein the computer subsystem is further configured for selecting a subset of defects detected on the wafer or another wafer from inspection results produced for the wafer or the other wafer, wherein the subset comprises one or more of the defects of interest and the nuisance defects, wherein the illumination subsystem is further configured to illuminate the defects in the subset on the wafer or the other wafer with the light having the illumination polarization, wherein the first and second side channels are further configured to detect light, due to the illumination, scattered from the defects in the subset for the two or more first polarization settings and the two or more second polarization settings, and wherein the computer subsystem is further configured for determining one or more characteristics of each of the defects included in the subset based on the output generated for at least two of the two or more first polarization settings and at least two of the two or more second polarization settings and selecting at least one of the two or more first and second polarization settings for inspection of wafers by the system based on the determined one or more characteristics.

43. The system of claim 42, wherein the computer subsystem is further configured for producing the inspection results for the wafer or the other wafer by performing a hot scan of the wafer or the other wafer with a nominal illumination polarization and nominal polarization settings of the first and second polarizing components.

44. The system of claim 42, wherein selecting the subset of defects comprises selecting at least one of the defects of interest and at least one of the nuisance defects from the inspection results based on region and intensity.

45. The system of claim 42, wherein the one or more characteristics comprise one or more of defect intensity, defect local noise, and signal-to-noise ratio, and wherein the one or more characteristics are determined as a function of at least two of the two or more first polarization settings and as a. function of at least two of the two or more second polarization settings.

46. The system of claim 42, wherein determining the one or more characteristics comprises normalizing the one or more characteristics to values for the one or more characteristics determined for nominal polarization settings of the first and second polarizing components.

47. The system of claim 42, wherein selecting the at least one of the two or more first or second polarization settings for the inspection comprises comparing the one or more characteristics determined for the one or more of the defects of interest to the one or more characteristics determined for the nuisance defects.

48. A method for detecting defects on a wafer, comprising:
illuminating the wafer with light having an illumination polarization;
detecting light scattered from the wafer due to said illuminating with first and second side channels of an inspection system and generating output responsive to the detected light;
prior to said detecting, directing the light from the wafer detected by the first side channel through a first polarizing component and directing the light from the wafer detected by the second side channel through a second polarizing component, wherein the first and second polarizing components are configured to have first and second detection polarizations, respectively, that are selected from two or more first and second polarization settings for the first and second polarizing components, respectively, wherein the two or more first polarization settings comprise at least one first detection polarization that is asymmetric to at least one second detection polarization included in the two or more second polarization settings, wherein the first detection polarization results in the output generated by the first side channel being sensitive to defects of interest and nuisance defects, and wherein the second detection polarization results in the output generated by the second side channel being sensitive to the nuisance defects but not the defects of interest; and
detecting defects on the wafer based on the output generated by at least one of the first and second side channels, wherein detecting the defects comprises identifying the defects that are detected with both the output of the first and second side channels as the nuisance defects.

* * * * *